United States Patent
Eyre

(10) Patent No.: US 6,602,980 B1
(45) Date of Patent: Aug. 5, 2003

(54) COLLAGEN TYPE III SYNTHETIC PEPTIDES FOR COLLAGEN RESORPTION ASSAYS

(75) Inventor: David R. Eyre, Seattle, WA (US)

(73) Assignee: Washington Research Foundation, Seattle, WA (US)

(*) Notice: Subject to any disclaimer, the term of this patent is extended or adjusted under 35 U.S.C. 154(b) by 0 days.

(21) Appl. No.: 10/009,999

(22) PCT Filed: Dec. 10, 1999

(86) PCT No.: PCT/US99/29357
§ 371 (c)(1),
(2), (4) Date: Jul. 1, 2002

(87) PCT Pub. No.: WO00/79284
PCT Pub. Date: Dec. 28, 2000

Related U.S. Application Data

(63) Continuation of application No. 09/385,740, filed on Aug. 30, 1999, now Pat. No. 6,348,320, which is a continuation of application No. 09/335,098, filed on Jun. 17, 1999, now Pat. No. 6,255,056.
(60) Provisional application No. 60/142,675, filed on Jul. 7, 1999, provisional application No. 60/142,274, filed on Jul. 2, 1999, and provisional application No. 60/141,574, filed on Jun. 29, 1999.

(51) Int. Cl.$^7$ .............................................. A61K 38/00
(52) U.S. Cl. ....................... 530/326; 530/327; 530/328; 530/356; 435/7.1
(58) Field of Search .................. 530/326, 327, 530/328, 356; 435/7.1

(56) References Cited

U.S. PATENT DOCUMENTS

| | | |
|---|---|---|
| 4,312,853 A | 1/1982 | Timpl |
| 4,504,587 A | 3/1985 | Timpl et al. |
| 4,628,027 A | 12/1986 | Gay |
| 4,973,666 A | 11/1990 | Eyre |
| 5,140,103 A | 8/1992 | Eyre |
| 5,300,434 A | 4/1994 | Eyre |
| 5,316,914 A | 5/1994 | Oshima et al. |
| 5,320,970 A | 6/1994 | Eyre |
| 5,342,756 A | 8/1994 | Risteli et al. |
| 5,702,909 A | 12/1997 | Eyre |
| 5,817,755 A | 10/1998 | Eyre et al. |

FOREIGN PATENT DOCUMENTS

| | | |
|---|---|---|
| CA | 1287801 | 8/1991 |
| EP | 0 089 008 A2 | 9/1983 |
| EP | 0 289 930 A2 | 11/1988 |
| EP | 0 298 210 A2 | 1/1989 |
| EP | 0 304 292 A2 | 2/1989 |
| EP | 0 339 443 A2 | 11/1989 |
| EP | 0 505 210 A2 | 9/1992 |
| EP | 0 699 752 A2 | 3/1996 |
| EP | 0 718 309 A1 | 6/1996 |
| GB | 2 205 643 A | 12/1988 |
| WO | WO 88/08980 A1 | 11/1988 |
| WO | WO 89/04491 A1 | 5/1989 |
| WO | WO 89/12824 A1 | 12/1989 |
| WO | WO 91/08478 A3 | 6/1991 |
| WO | WO 92/21698 A1 | 12/1992 |
| WO | WO 94/03813 A1 | 2/1994 |
| WO | WO 94/14070 | 6/1994 |
| WO | WO 94/14844 A1 | 7/1994 |
| WO | WO 94/18563 A1 | 8/1994 |
| WO | WO 95/04282 A1 | 2/1995 |
| WO | WO 95/08115 A1 | 3/1995 |
| WO | WO 96/12193 | 4/1996 |
| WO | WO 96/36645 | 11/1996 |

OTHER PUBLICATIONS

Ala–Kokko, L., et al., "Structure of cDNA Clones Coding for the Entire Preproα1 (III) Chain of Human Type III Precollagen," *Biochem. J.* 260:509–516, 1989.

Seibel, M.J., "Komponenten der extrazellulären Gewebematrix als potentialle . . . Marker des Bindegewebs–, Knorpel–und Knochenmetabolismus bei Erkrankungen des Bewegungsapparates," *Z. Rheumatol.* 48:6–18, 1989.

Niemelá, O., "Radioimmunoassays for Type III Procollagen Amino–Terminal Peptides in Humans," *Clin. Chem.* 31(8):1301–1304, 1985.

Loid, H.R., et al., "Molecular Cloning and Carboxyl–Propeptide Analysis of Human Type III Procollagen," *Nucleic Acids Research* 12(24):9383–9394, 1984.

Pierard, D., et al., "Radioimmunoassay for the Amino–Terminal Sequences of Type III Procollagen in Human Body Fluids Measuring Fragmented Precursor Sequences," *Analytical Biochem.* 141:127–136, 1984.

Rohde, H., et al., "Radioimmunoassay for Type III Procollagen Peptide and Its Application to Human Liver Disease," *Euro. J. Clin. Invest.* 9:451–459, 1979.

Eyre, D.R., "Cross–Linking in Collagen and Elastin," *Ann. Rev. Biochem.* 53:717–748, 1984.

Hasselbach, H., et al., "Procollagen Type III Aminoterminal Peptide in Serum in Idiopathic Myelofibrosis and Allied Conditions: Relation to Disease Activity and Effect of Chemotherapy," *Am. J. Hematol.* 33:18–26, 1990.

Hanson, D.A., et al., "A Specific Immunoassay for Monitoring Human Bone Resorption: Quantitation of Type I Collagen Cross–Linked N–Telopeptides in Urine," *J. Bone and Min. Res.* 7(11):1251–1258, 1992.

(List continued on next page.)

Primary Examiner—Jeffrey Stucker
(74) Attorney, Agent, or Firm—Christensen O'Connor Johnson Kindness PLLC

(57) ABSTRACT

Peptides synthesized to match N-telopeptide components of type III collagen degradation products in body fluids, selected from among DVKSGVAVGG (SEQ ID NO 33), YDVKSGVAVGG (SEQ ID NO 34), SYDVKSGVAVGG (SEQ ID NO 35), DSYDVKSGVAVGG (SEQ ID NO 36), JYDSYDVKSGVAVGG (SEQ ID NO 37), and KSGVAVGG (SEQ ID NO 45) are claimed. The peptides are useful as immunogens and antigens in collagen resorption assays.

1 Claim, No Drawings

OTHER PUBLICATIONS

Lane, J.M., et al., "Immunofluorescent Localization of Structural Collagen Types in Endochondral Fracture Healing," *Orthopaedic Transactions VI*(2):236, 1982.

Kühn, K., "The Classical Collagens: Types I, II, and III," in *Structure and Function of Collagen Types,* Academic Press, Inc., 1987, pp. 1–42.

Stoltenberg, M., et al., "Intra–Articular and Circulating Levels of Type I and III Collagen Markers in Inflammatory and Degenerative Joint Disease," *Acta. Orthop. Scand.* 66(Suppl 266):147–148, 1995.

Eyre, D.R., et al., "Cross–Linked Telopeptides From Collagen Types I, II and III in Human Urine," ASBMR Meeting, Sep. 1996.

Horslev–Petersen, K., "Circulating Extracellular Matrix Components as Markers for Connective Tissue Response to Inflammation," *Danish Med. Bul. 37*(4):308–329, 1990.

Hanson, D.A., and D.R. Eyre, "Molecular Site Specificity of Pyridinoline and Pyrrole Cross–Links in Type I Collagen of Human Bone," *J. Biol. Chem. 271*(43):26508–26516, 1996.

Myllylä, R., et al., "Markers of Collagen Metabolism in Sera of Patients With Various Rheumatic Diseases," *Clinica Chimica Acta 183*:243–252, 1989.

Macarak, E.J., et al., "Production and Characterization of a Monoclonal Antibody to Human Type III Collagen," *J. Histochem. Cytochem.* 34(8):1003–1011, 1986, in *Chem. Abstracts 105*:95762y, 1986.

Macarak, E.J., et al., "Production and Characterization of a Monoclonal Antibody to Human Type III Collagen," *J. Histochem. and Cytochem.* 34(8):1003–1011, 1986.

Otter, A., et al., "Conformational Analysis of the Type II and III Collagen α–1 Chain N–Telopeptides by Proton–NMR Spectroscopy and Restrained Molecular Mechanics Calculations," *Biopolymers 33*(9):1443–1459, 1993, in *Chem. Abstracts 119*:264860a, 1993.

Gosslau, B., and H.–J. Barrach, "Enzyme–Linked Immunosorbent Microassay for Quantification of Specific Antibodies to Collagen Type I, II, and III," *J. Immunol. Meth.* 29:71–77, 1979.

Atley, L., et al., "A Selective Inhibitor of Collagenase–3 Blocks the Release of Hydroxyproline and a Metalloproteinase Specific Neopitope, Coll II CTx, From Bovine Cartilege Exposed to IL–1α," *Arth. Rheum. 40*(9S):584, 1997.

Niemelä, O., et al., "Heterogeneity of the Antigens Related to the Aminoterminal Propeptide of Type III Procollagen in Human Serum," *Clinica Chimica Acta 124*:39–44, 1982.

Atley, L.M., et al., "Matrix Metalloproteinase–Mediated Release of Immunoreactive Telopeptide From Cartilage Type II Collagen," *44th Annual Meeting, Orthop. Res. Soc.,* New Orleans, Mar. 16–19, 1998.

Moskowitz, R.W., et al., "Type II Collagen C–Telopeptide 2B4 Epitope Is a Marker for Cartilage Degradation in Familial Osteoarthritis," *Meeting of Amer. Coll. Rheum.,* San Diego, Nov. 8–12, 1998.

Eyre, D.R., et al., "Biochemical Markers of Bone and Cartilage Collagen Degradation," *Combined Orthopaedic Research Societies Meeting,* Vittel, France, Sep. 28–30, 1998.

Sheridan, C., "Osteometer Targets Collagen for Osteoporosis, Arthritis Tests," *BioWorld International,* Dec. 3, 1997, p. 3.

Atley, L.M., et al., "Collagen Type II Cross–Linked Telopeptides, a Promising Marker for Cartilage Degradation in Arthritis," *Combined Orthopaedic Research Societies Meeting,* Hamamatsu, Japan, 1998.

Otter, A., et al., "Conformational Analysis of the Type II and Type III Collagen α–1 Chain N–Telopeptides by H–NMR Stpectroscopy and Restrained Molecular Mechanics Calculations," *Biopolymers 33*:1443–1459, 1993.

SEQUENCE LISTING

```
<160> NUMBER OF SEQ ID NOS: 45

<210> SEQ ID NO 1
<211> LENGTH: 5
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 1

Glu Lys Gly Pro Asp
1               5

<210> SEQ ID NO 2
<211> LENGTH: 6
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 2

Glu Lys Gly Pro Asp Pro
1               5

<210> SEQ ID NO 3
```

```
<211> LENGTH: 7
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 3

Glu Lys Gly Pro Asp Pro Leu
1               5

<210> SEQ ID NO 4
<211> LENGTH: 14
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 4

Ala Phe Ala Gly Leu Gly Pro Arg Glu Lys Gly Pro Asp Pro
1               5                   10

<210> SEQ ID NO 5
<211> LENGTH: 20
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 5

Ala Phe Ala Gly Leu Gly Pro Arg Glu Lys Gly Pro Asp Pro Leu Gln
1               5                   10                  15

Tyr Met Arg Ala
            20

<210> SEQ ID NO 6
<211> LENGTH: 16
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 6

Ala Phe Ala Gly Leu Gly Pro Arg Glu Lys Gly Pro Asp Pro Leu Gln
1               5                   10                  15

<210> SEQ ID NO 7
<211> LENGTH: 17
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 7

Ala Phe Ala Gly Leu Gly Pro Arg Glu Lys Gly Pro Asp Pro Leu Gln
1               5                   10                  15

Tyr
```

<210> SEQ ID NO 8
<211> LENGTH: 6
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 8

Leu Gln Tyr Met Arg Ala
1               5

<210> SEQ ID NO 9
<211> LENGTH: 4
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 9

Tyr Met Arg Ala
1

<210> SEQ ID NO 10
<211> LENGTH: 8
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 10

Glu Lys Gly Pro Asp Pro Leu Gln
1               5

<210> SEQ ID NO 11
<211> LENGTH: 10
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 11

Leu Gly Pro Arg Glu Lys Gly Pro Asp Pro
1               5                   10

<210> SEQ ID NO 12
<211> LENGTH: 12
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 12

Leu Gly Pro Arg Glu Lys Gly Pro Asp Pro Leu Gln
1               5                   10

<210> SEQ ID NO 13
<211> LENGTH: 13
<212> TYPE: PRT
<213> ORGANISM: Homo sapiens

```
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 13

Leu Gly Pro Arg Glu Lys Gly Pro Asp Pro Leu Gln Tyr
1               5                   10

<210> SEQ ID NO 14
<211> LENGTH: 13
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 14

Phe Ala Gly Leu Gly Pro Arg Glu Lys Gly Pro Asp Pro
1               5                   10

<210> SEQ ID NO 15
<211> LENGTH: 15
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 15

Phe Ala Gly Leu Gly Pro Arg Glu Lys Gly Pro Asp Pro Leu Gln
1               5                   10                  15

<210> SEQ ID NO 16
<211> LENGTH: 16
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 16

Phe Ala Gly Leu Gly Pro Arg Glu Lys Gly Pro Asp Pro Leu Gln Tyr
1               5                   10                  15

<210> SEQ ID NO 17
<211> LENGTH: 18
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 17

Ile Asp Met Ser Ala Phe Ala Gly Leu Gly Pro Arg Glu Lys Gly Pro
1               5                   10                  15

Asp Pro

<210> SEQ ID NO 18
<211> LENGTH: 20
<212> TYPE: PRT
<213> ORGANISM: Homo sapiens
<220> FEATURE:
<221> NAME/KEY: MISC_FEATURE
```

```
<223> OTHER INFORMATION: synthetic peptide corresponding to carboxy-
      terminal telopeptide sequence of human type II collagen

<400> SEQUENCE: 18

Ile Asp Met Ser Ala Phe Ala Gly Leu Gly Pro Arg Glu Lys Gly Pro
1               5                   10                  15

Asp Pro Leu Gln
            20

<210> SEQ ID NO 19
<211> LENGTH: 21
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 19

Ile Asp Met Ser Ala Phe Ala Gly Leu Gly Pro Arg Glu Lys Gly Pro
1               5                   10                  15

Asp Pro Leu Gln Tyr
            20

<210> SEQ ID NO 20
<211> LENGTH: 11
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type II collagen

<400> SEQUENCE: 20

Glu Lys Gly Pro Asp Pro Leu Gln Tyr Met Arg
1               5                   10

<210> SEQ ID NO 21
<211> LENGTH: 7
<212> TYPE: PRT
<213> ORGANISM: Homo sapiens
<220> FEATURE:
<221> NAME/KEY: MISC_FEATURE
<223> OTHER INFORMATION: synthetic peptide corresponding to amino-
      terminal telopeptide sequence of human type II collagen

<400> SEQUENCE: 21

Asp Glu Lys Ala Gly Gly Ala
1               5

<210> SEQ ID NO 22
<211> LENGTH: 8
<212> TYPE: PRT
<213> ORGANISM: Homo sapiens
<220> FEATURE:
<221> NAME/KEY: MISC_FEATURE
<223> OTHER INFORMATION: synthetic peptide corresponding to amino-
      terminal telopeptide sequence of human type II collagen

<400> SEQUENCE: 22

Asp Glu Lys Ala Gly Gly Ala Gln
1               5

<210> SEQ ID NO 23
<211> LENGTH: 9
<212> TYPE: PRT
<213> ORGANISM: Homo sapiens
```

```
<220> FEATURE:
<221> NAME/KEY: MISC_FEATURE
<223> OTHER INFORMATION: synthetic peptide corresponding to amino-
      terminal telopeptide sequence of human type II collagen

<400> SEQUENCE: 23

Asp Glu Lys Ala Gly Gly Ala Gln Leu
1               5

<210> SEQ ID NO 24
<211> LENGTH: 8
<212> TYPE: PRT
<213> ORGANISM: Homo sapiens
<220> FEATURE:
<221> NAME/KEY: MISC_FEATURE
<223> OTHER INFORMATION: synthetic peptide corresponding to amino-
      terminal telopeptide sequence of human type II collagen

<400> SEQUENCE: 24

Phe Asp Glu Lys Ala Gly Gly Ala
1               5

<210> SEQ ID NO 25
<211> LENGTH: 9
<212> TYPE: PRT
<213> ORGANISM: Homo sapiens
<220> FEATURE:
<221> NAME/KEY: MISC_FEATURE
<223> OTHER INFORMATION: synthetic peptide corresponding to amino-
      terminal telopeptide sequence of human type II collagen

<400> SEQUENCE: 25

Phe Asp Glu Lys Ala Gly Gly Ala Gln
1               5

<210> SEQ ID NO 26
<211> LENGTH: 10
<212> TYPE: PRT
<213> ORGANISM: Homo sapiens
<220> FEATURE:
<221> NAME/KEY: MISC_FEATURE
<223> OTHER INFORMATION: synthetic peptide corresponding to amino-
      terminal telopeptide sequence of human type II collagen

<400> SEQUENCE: 26

Phe Asp Glu Lys Ala Gly Gly Ala Gln Leu
1               5                   10

<210> SEQ ID NO 27
<211> LENGTH: 13
<212> TYPE: PRT
<213> ORGANISM: Homo sapiens
<220> FEATURE:
<221> NAME/KEY: MISC_FEATURE
<223> OTHER INFORMATION: synthetic peptide corresponding to amino-
      terminal telopeptide sequence of human type II collagen

<400> SEQUENCE: 27

Gly Gly Phe Asp Glu Lys Ala Gly Gly Ala Gln Leu Gly
1               5                   10

<210> SEQ ID NO 28
<211> LENGTH: 16
<212> TYPE: PRT
<213> ORGANISM: Homo sapiens
<220> FEATURE:
<221> NAME/KEY: MISC_FEATURE
<223> OTHER INFORMATION: synthetic peptide corresponding to amino-
      terminal telopeptide sequence of human type II collagen
```

```
<220> FEATURE:
<221> NAME/KEY: MISC_FEATURE
<222> LOCATION: (1)..(1)
<223> OTHER INFORMATION: Xaa is pyroglutamic acid

<400> SEQUENCE: 28

Xaa Met Ala Gly Gly Phe Asp Glu Lys Ala Gly Gly Ala Gln Leu Gly
1               5                   10                  15

<210> SEQ ID NO 29
<211> LENGTH: 17
<212> TYPE: PRT
<213> ORGANISM: Homo sapiens
<220> FEATURE:
<221> NAME/KEY: MISC_FEATURE
<223> OTHER INFORMATION: synthetic peptide corresponding to amino-
      terminal telopeptide sequence of human type II collagen
<220> FEATURE:
<221> NAME/KEY: MISC_FEATURE
<222> LOCATION: (1)..(1)
<223> OTHER INFORMATION: Xaa is pyroglutamic acid

<400> SEQUENCE: 29

Xaa Met Ala Gly Gly Phe Asp Glu Lys Ala Gly Gly Ala Gln Leu Gly
1               5                   10                  15

Val

<210> SEQ ID NO 30
<211> LENGTH: 12
<212> TYPE: PRT
<213> ORGANISM: Homo sapiens
<220> FEATURE:
<221> NAME/KEY: MISC_FEATURE
<223> OTHER INFORMATION: synthetic peptide corresponding to amino-
      terminal telopeptide sequence of human type II collagen

<400> SEQUENCE: 30

Phe Asp Glu Lys Ala Gly Gly Ala Gln Leu Gly Val
1               5                   10

<210> SEQ ID NO 31
<211> LENGTH: 11
<212> TYPE: PRT
<213> ORGANISM: Homo sapiens
<220> FEATURE:
<221> NAME/KEY: MISC_FEATURE
<223> OTHER INFORMATION: synthetic peptide corresponding to amino-
      terminal telopeptide sequence of human type II collagen

<400> SEQUENCE: 31

Asp Glu Lys Ala Gly Gly Ala Gln Leu Gly Val
1               5                   10

<210> SEQ ID NO 32
<211> LENGTH: 18
<212> TYPE: PRT
<213> ORGANISM: Homo sapiens
<220> FEATURE:
<221> NAME/KEY: MISC_FEATURE
<223> OTHER INFORMATION: synthetic peptide corresponding to amino-
      terminal telopeptide sequence of human type III collagen
<220> FEATURE:
<221> NAME/KEY: MISC_FEATURE
<222> LOCATION: (1)..(1)
<223> OTHER INFORMATION: Xaa is pyroglutamic acid

<400> SEQUENCE: 32

Xaa Tyr Asp Ser Tyr Asp Val Lys Ser Gly Val Ala Val Gly Gly Leu
1               5                   10                  15
```

Ala Gly

```
<210> SEQ ID NO 33
<211> LENGTH: 10
<212> TYPE: PRT
<213> ORGANISM: Homo sapiens
<220> FEATURE:
<221> NAME/KEY: MISC_FEATURE
<223> OTHER INFORMATION: synthetic peptide corresponding to amino-
      terminal telopeptide sequence of human type III collagen

<400> SEQUENCE: 33

Asp Val Lys Ser Gly Val Ala Val Gly Gly
1               5                   10

<210> SEQ ID NO 34
<211> LENGTH: 11
<212> TYPE: PRT
<213> ORGANISM: Homo sapiens
<220> FEATURE:
<221> NAME/KEY: MISC_FEATURE
<223> OTHER INFORMATION: synthetic peptide corresponding to amino-
      terminal telopeptide sequence of human type III collagen

<400> SEQUENCE: 34

Tyr Asp Val Lys Ser Gly Val Ala Val Gly Gly
1               5                   10

<210> SEQ ID NO 35
<211> LENGTH: 12
<212> TYPE: PRT
<213> ORGANISM: Homo sapiens
<220> FEATURE:
<221> NAME/KEY: MISC_FEATURE
<223> OTHER INFORMATION: synthetic peptide corresponding to amino-
      terminal telopeptide sequence of human type III collagen

<400> SEQUENCE: 35

Ser Tyr Asp Val Lys Ser Gly Val Ala Val Gly Gly
1               5                   10

<210> SEQ ID NO 36
<211> LENGTH: 13
<212> TYPE: PRT
<213> ORGANISM: Homo sapiens
<220> FEATURE:
<221> NAME/KEY: MISC_FEATURE
<223> OTHER INFORMATION: synthetic peptide corresponding to amino-
      terminal telopeptide sequence of human type III collagen

<400> SEQUENCE: 36

Asp Ser Tyr Asp Val Lys Ser Gly Val Ala Val Gly Gly
1               5                   10

<210> SEQ ID NO 37
<211> LENGTH: 15
<212> TYPE: PRT
<213> ORGANISM: Homo sapiens
<220> FEATURE:
<221> NAME/KEY: MISC_FEATURE
<223> OTHER INFORMATION: synthetic peptide corresponding to amino-
      terminal telopeptide sequence of human type III collagen
<220> FEATURE:
<221> NAME/KEY: MISC_FEATURE
<222> LOCATION: (1)..(1)
<223> OTHER INFORMATION: Xaa is pyroglutamic acid

<400> SEQUENCE: 37
```

```
Xaa Tyr Asp Ser Tyr Asp Val Lys Ser Gly Val Ala Val Gly Gly
1               5                   10                  15
```

<210> SEQ ID NO 38
<211> LENGTH: 15
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type III collagen

<400> SEQUENCE: 38

```
Gln Tyr Asp Ser Tyr Asp Val Lys Ser Gly Val Ala Val Gly Gly
1               5                   10                  15
```

<210> SEQ ID NO 39
<211> LENGTH: 6
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type III collagen

<400> SEQUENCE: 39

```
Glu Lys Ala Gly Gly Phe
1               5
```

<210> SEQ ID NO 40
<211> LENGTH: 8
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type III collagen

<400> SEQUENCE: 40

```
Ile Gly Gly Glu Lys Ala Gly Gly
1               5
```

<210> SEQ ID NO 41
<211> LENGTH: 9
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type III collagen

<400> SEQUENCE: 41

```
Ile Gly Gly Glu Lys Ala Gly Gly Phe
1               5
```

<210> SEQ ID NO 42
<211> LENGTH: 11
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type III collagen

<400> SEQUENCE: 42

```
Ile Ala Gly Ile Gly Gly Glu Lys Ala Gly Gly
1               5                   10
```

-continued

```
<210> SEQ ID NO 43
<211> LENGTH: 12
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type III collagen

<400> SEQUENCE: 43

Ile Ala Gly Ile Gly Gly Glu Lys Ala Gly Gly Phe
1               5                   10

<210> SEQ ID NO 44
<211> LENGTH: 5
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type III collagen

<400> SEQUENCE: 44

Glu Lys Ala Gly Gly
1               5

<210> SEQ ID NO 45
<211> LENGTH: 8
<212> TYPE: PRT
<213> ORGANISM: Homo sapiens
<220> FEATURE:
<221> NAME/KEY: MISC_FEATURE
<223> OTHER INFORMATION: synthetic peptide corresponding to carboxy-
      terminal telopeptide sequence of human type III collagen

<400> SEQUENCE: 45

Lys Ser Gly Val Ala Val Gly Gly
1               5
```

COLLAGEN TYPE III SYNTHETIC PEPTIDES FOR COLLAGEN RESORPTION ASSAYS

This is a national stage application PCT/US99/29357 filed Dec. 10, 1999, which is a continuation of Ser. No. 09/335,098, filed Jun. 17, 1999, now U.S. Pat. No. 6,255,056, which claims benefit of No. 60/141,574, filed Jun. 29, 1999, and No. 60/142,274, filed Jul. 2, 1999, and No. 60/142,675, filed Jul. 7, 1999, and is a continuation of Ser. No. 09/385,740, filed Aug. 30, 1999, now U.S. Pat. No. 6,348,320.

This invention was made with government support under one or more of grants AR 37318 and AR 36794 awarded by the National Institutes of Health. The government has certain rights in the invention.

FIELD OF THE INVENTION

The invention relates to assays for detecting cross-linked telopeptide analytes indicative of type II collagen (cartilage) resorption in vivo, and in particular provides immunoassays for measuring and distinguishing between resorption of non-mineralized cartilage and mineralized cartilage, and for measuring total cartilage resorption in vivo.

BACKGROUND OF THE INVENTION

Reference is made to the applicant's prior U.S. Pat. Nos. 4,973,666, 5,140,103, 5,300,434, 5,320,970, 5,817,755, and 5,702,909, which are incorporated by reference herein.

Immunoassays are known for detecting telopeptide analytes indicative of collagen resorption in vivo. Examples of such type I collagen assays for measuring bone resorption include: WO 89/04491 (Eyre); WO 89/12824 (Robins); WO 91/08478 (Eyre); EP 0505210 A2 (Risteli & Risteli); WO 92/21698 (Eyre); WO 94/03813 (Naser et al.); WO 94/14844 (Baylink); WO 95/04282 (Naser et al.); WO 95/08115 (Qvist & Bonde); WO 96/12193 (Bonde & Qvist); EP 0718309 A1 (Naser et al.); and WO 96/36645 (Eyre et al.).

Examples of type II collagen telopeptide assays for measuring cartilage resorption include WO 91/08478 (Eyre); WO 95/08115 (Qvist & Bonde); and WO 96/12193 (Bonde & Qvist).

Examples of type III collagen telopeptide assays include WO 88/08980 (Risteli & Risteli) and WO 91/08478 (Eyre).

The following patent disclosures are also of interest: U.S. Pat. No. 4,628,027 (Gay) discloses in vitro diagnostic methods using monoclonal antibodies against connective tissue proteins. U.S. Pat. No. 5,316,914 (Oshima et al.) discloses an enzyme sandwich immunoassay of human type III, IV, and VI collagens applicable to diagnosis of hepatic diseases. WO 94/14070 (Poole & Hollander) discloses an immunoassay for the measurement of collagen cleavage in cartilage. WO 94/18563 (Barrach et al.) discloses sandwich immunoassay methods for detecting type II collagen derived peptides associated with arthritis.

Of particular interest is the applicant's prior international publication, WO 91/0478, which discloses the following urinary resorption products of type II collagen:

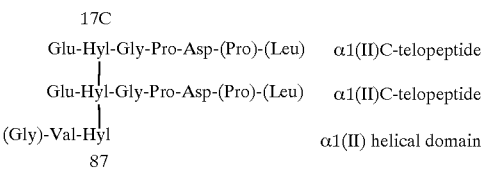

wherein the parentheses indicate optional amino acid residues, and the cross-linking residue depicted as Hyl-Hyl-Hyl is hydroxylysyl pyridinoline (HP), a natural 3-hydroxypyridinium residue present in mature collagen fibrils of various tissues. These analytes derive from the C-terminal cross-linked telopeptide domain of type II collagen and so are collectively referred to herein as "col2CTx".

The present disclosure also adopts the one-letter symbol form of amino acid shorthand; thus, the Glu-Hyl-Gly-Pro-Asp-(Pro)-(Leu) telopeptide components of the analytes shown above are referred to hereinafter as EKGPD (SEQ ID NO:1), EKGPDP (SEQ ID NO:2), and EKGPDPL (SEQ ID NO:3). Furthermore, as used herein the symbol "K" represents either lysine, in the case of linear peptides, or a cross-linking 3-hydroxypyridinium residue selected from among hydroxylysyl pyridinoline (HP) and lysyl pyridinoline (LP).

The applicant and colleagues have also described col2CTx in recent abstracts:

Eyre et al., Bone Miner. Res. 11(S1): S413, 1996, describes cross-linked telopeptides from collagen types I, II, and III in human urine.

Atley et al., Arth. Rheum. 40(9S):584, 1997, reports that RS-130830, a selective inhibitor of collagenase-3, blocks the release of hydroxyproline and a metalloproteinase (MMP) specific neoepitope, col2CTx, from bovine cartilage exposed to IL-1α.

Atley et al., Trans. Orthop. Res. Soc., New Orleans, 1998, reports matrix metalloproteinase-mediated release of immunoreactive telopeptides from cartilage type II collagen. The aim of this study was to evaluate whether an immunoassay based on a monoclonal antibody (mAb) 2B4, which recognizes a domain of the α1(II) C-telopeptide EKGPDP, measures MMP cleavage products in cartilage. Referring to FIG. 1, mAb 2B4 recognizes the in vitro product of matrilysin digestion AFAGLGPREKGPDP (SEQ ID NO:4) of synthetic peptide AFAGLGPREKGPDPLQYMRA (SEQ ID NO:5), but not AFAGLGPREKGPDPLQ (SEQ ID NO:6), AFAGLGPREKGPDPLQY (SEQ ID NO:7), LQYMRA (SEQ ID NO:8), or YMRA (SEQ ID NO:9). The authors also noted detection of mAb 2B4 immunoreactivity in synovial fluid, serum, and urine. They concluded that this 2B4 epitope has the potential to be a useful marker of type II collagen resorption in vivo.

Moskowitz et al., Amer. Coll. Rheum. San Diego, Calif., Nov. 8–12, 1998, reports that the type II collagen C-telopeptide 2B4 epitope is a marker for cartilage resorption in familial osteoarthrosis.

Eyre et al., 6th International Meeting on Chemistry and Biology of Mineralized Tissues, Vittel, France, September 1998, discusses biochemical markers of bone and collagen degradation, including a cross-linked telopeptide product of type II collagen degradation in urine (col2CTx).

Atley et al., Third Combined Orthopaedic Research Societies Meeting, Hamamatsu, Japan, September 1998, discusses collagen type II cross-linked telopeptides, a promising marker for cartilage degradation in arthritis.

In addition, monoclonal antibodies to the C-telopeptide of type II collagen as diagnostic markers for rheumatoid arthritis are reportedly under development at Osteometer Biotech A/S. Bio World International, page 3, Dec. 3, 1997.

The entire disclosures of the prior scientific and patent publications cited in this patent application are incorporated by reference herein.

SUMMARY OF THE INVENTION

The invention provides improved assays for measuring type II collagen (cartilage) resorption in vivo. The subject immunoassays are useful for distinguishing between resorption of non-mineralized cartilage and mineralized cartilage, and for measuring total cartilage resorption in vivo. The disclosed immunoassays employ either one or a combination of two antibodies. A first antibody binds to DEKAGGA (SEQ ID NO:21) but not to GGFDEKAGGAQLG (SEQ ID NO:27), where the K symbols refer to lysine residues and/or preferably to cross-linking 3-hydroxypyridinium residues. Measurement of analyte binding to the first antibody in serum provides an indication of non-mineralized cartilage resorption in vivo.

A second antibody binds to GGFDEKAGGAQLG but not to DEKAGGA, where the K symbols also preferably refer to cross-linking 3-hydroxypyridinium residues. Measurement of analyte binding to the second antibody in serum provides an indication of mineralized cartilage resorption in vivo.

An indication of total (non-mineralized and mineralized) cartilage resorption in vivo is provided by either measurement of analyte binding to the first antibody in urine, or by measurement of the total analyte binding to the first and second antibodies in serum.

The subject cartilage markers are preferably measured in conjunction with bone collagen resorption markers selected from among amino-terminal telopeptides of type I collagen, carboxy-terminal telopeptides of type I collagen, and free lysyl pyridinoline (deoxypyridinoline) cross-links.

DETAILED DESCRIPTION OF THE PREFERRED EMBODIMENT

By way of introduction, the monoclonal antibody 2B4 recognizes a C-terminal epitope in the sequence EKGPDP. The antibody requires the C-terminal proline to be free for any binding (i.e., Pro-COOH) and prefers K to be derivatized (e.g., cross-linked) through its side-chain (epsilon) amino group. The presence of extra amino acids C-terminal to the proline prevents mAb 2B4 binding to this peptide domain.

Various matrix metalloproteinases (MMPs) including collagenases (MMP1 and MMP13), gelatinases (MMP2 and 9), stromelysin (MMP3), and matrilysin (MMP7) can generate the mAb 2B4 epitope from cartilage type II collagen or a synthetic C-telopeptide domain (AFAGLGPREKGPDPLQYMRA). Matrilysin (MMP7) is the most potent based on in vitro studies with the recombinant enzymes.

Cathepsin K, however, is unable to cleave the P—L bond required for 2B4 epitope release, but generates a longer fragment, EKGPDPLQ (SEQ ID NO:10). This is significant because cathepsin K is a protease expressed essentially only by osteoclasts and is the key enzyme responsible for the resorption of the calcified collagen when osteoclasts resorb bone. Osteoclasts (or a very similar cell) are also responsible for degrading calcified cartilage. Calcified cartilage is formed transiently in the growth plates of growing animals and is also present in the adult skeleton at the interfaces between bone and cartilage in all types of joints. In arthritis, accelerated resorption and bony remodeling will result in extensive resorption of calcified cartilage by osteoclasts. This process can release into the bloodstream collagen type II C-telopeptides (EKGPDPLQ) that are not recognized by 2B4.

Since the urinary form of the type II collagen telopeptide analyte is EKGPDP or smaller, proteases in the kidney and/or liver remove substantially all of the C-terminal—LQ before release into the urine. Therefore, two sources of immunoreactive col2CTx are can be defined: (1) direct generation by chondrocytes activated to degrade their matrix collagen by MMPs, and (2) secondary generation in the kidney and/or liver from the circulating products of osteoclastic resorption of calcified cartilage.

In arthritis (rheumatoid arthritis (RA) and osteoarthritis (OA)) MMPs are known to be key agents in the destruction of the collagenous matrices of joint cartilages. In both forms of arthritis, bone structure is also greatly affected. In RA, osteoporosis is a common consequence both directly from the disease process itself through the effects of inflammatory cytokines and as a side effect of corticosteroid therapy. The accelerated bone resorption will be most pronounced in involved joints and will include removal of the calcified cartilage underlying joint surfaces. In OA, osteophytes (bony outgrowths) often feature prominently in the joint pathology. Here, too, calcified cartilage will be formed and then degraded (the latter by osteoclasts) as part of osteophyte growth. Therefore to monitor and manage both major forms of arthritis it would be desirable to differentially measure MMP-mediated and osteoclast-mediated (cathepsin K) collagen type II destruction. In blood or synovial fluid, measuring col2CTx (EKGPDP) can index the former activity, whereas measuring the osteoclast product (EKGPDPLQ) in blood can index the latter. In addition, urinary col2CTx can provide an index of total resorption (both non-mineralized and mineralized cartilage). Such urine assays preferably include the steps of determining the creatinine content of the urine sample and correlating the ratio of the detected binding of the antibody to the creatinine content in order to provide a urinary index of total type II collagen resorption independent of urine volume.

The subject differential measurements of EKGPDP and EKGPDPLQ immunoreactivities have diagnostic value in the assessment of disease activity in the individual patient. In combination with measurement of a type I collagen marker to assess total bone resorption activity, and/or measurement of a type III collagen marker to assess other sources of non-mineralized connective tissue breakdown, an appropriate therapy can be prescribed and its desired effect monitored. Similarly, such differential assays can be used to identify new drug candidates (in vitro and in animals) and to provide surrogate markers in clinical trials for demonstrating desired beneficial effects on target tissues and cellular processes.

Representative assays for type I collagen resorption markers for this purpose include amino-terminal telopeptides of type I collagen (Osteomark®, Ostex International, Seattle, Wash.), carboxy-terminal telopeptides of type I collagen (CrossLaps®, Osteometer Biotech, Herlev, Denmark), and free lysyl pyridinoline cross-links (Pyrilinks®-D, Metra Biosystems, Mountain View, Calif.).

Representative assays for type III collagen resorption markers include amino-terminal telopeptides of type III collagen and carboxy-terminal telopeptides of type III collagen. Such assays are disclosed in U.S. Pat. Nos. 5,532,169, 5,641,687, and U.S. Ser. No. 08/923,175. Type III collagen resorption markers can be used to assess vascular collagen degradation (atherosclerosis), lung tissue degradation (e.g., emphysema and other destructive lung diseases), muscle wastage, frailty syndromes of the elderly, liver disease, hyperthyroidism, secondary effects of diabetes on connective tissue, and other inflammatory and infectious conditions that accelerate total bone resorption activity.

The invention also provides antibodies directed against other cross-linked carboxy-telopeptide degradation products of type II collagen, as well as linear peptides (SEQ ID NOS 11–20) synthesized to match the telopeptide components of the degradation products, and assays for cartilage degradation using the antibodies and linear peptides.

| α1(II)C Telopeptide Sequence | SEQ ID NO | Body Fluid[1] | | |
|---|---|---|---|---|
| | | Synovial fluid | Blood | Urine |
| EKGPD | 1 | — | N | N + M |
| EKGPDP | 2 | N | N | N + M |
| EKGPDPL | 3 | N | N | N + M |
| EKGPDPLQ | 10 | — | M | — |
| LGPREKGPDP | 11 | N | N | — |
| LGPREKGPDPLQ | 12 | N | N | — |
| LGPREKGPDPLQY | 13 | N | N | — |
| FAGLGPREKGPDP | 14 | N | N | — |
| FAGLGPREKGPDPLQ | 15 | N | N | — |
| FAGLGPREKGPDPLQY | 16 | N | N | — |
| IDMSAFAGLGPREKGPDP | 17 | N | N | — |
| IDMSAFAGLGPREKGPDPLQ | 18 | N | N | — |
| IDMSAFAGLGPREKGPDPLQY | 19 | N | N | — |
| EKGPDPLQYMR | 20 | N | N | — |

[1]Cartilage Source:
N = non-mineralized cartilage;
M = mineralized cartilage;
N + M = total cartilage degradation; and
— = absent or only trace amounts.

The principal col2CTx degradation product is cross-linked EKGPDP. The further degradation product cross-linked EKGPD is usually present in urine in lower amounts. The cross-linked EKGPDPL degradation product is a minor component relative to cross-linked EKGPDP.

Higher than normal levels of cross-linked EKGPDPLQ in blood can indicate mineralized cartilage degradation associated with active osteophyte formation in osteoarthritis.

The telopeptide sequences represented by SEQ ID NOS 11–13 result from metalloproteinase (MMP) cleavage of the G-L bond at the amino end of the α1(II)C telopeptide (SEQ ID NO 5), in combination with MMP cuts of the P-L, Q-Y, or Y-M bonds at the carboxy end of the telopeptide. SEQ ID NOS 14–16 represent related telopeptides from MMP cleavage between the A-F bond. SEQ ID NOS 17–19 represent longer telopeptides from MMP cleavage between the G-I bond. The amino ends of these longer telopeptides are generally metabolized further in the lymph nodes, liver, and/or kidney.

The telopeptide sequence represented by SEQ ID NO 20 results from serine protease cleavage of the R-E bond amino terminal to the cross-linking K residue, in combination with serine protease cleavage of the R-A bond at the carboxy end of the telopeptide.

Such cross-linking degradation products of SEQ ID NOS 11–19 (wherein the two telopeptide components are independently selected from among SEQ ID NOS 11–19), and SEQ ID NO 20, generally result from degradation of non-mineralized cartilage and are primarily found in synovial fluid and blood, and to a lesser extent in urine. Higher than normal levels of these degradation products in body fluids indicate active cartilage degradation that may correlate with rheumatoid arthritis, osteoarthritis, and other arthritides.

The invention also provides antibodies directed against cross-linked amino-telopeptide degradation products of type II collagen, as well as linear peptides (SEQ ID NOS 21–31) synthesized to match the telopeptide components of the degradation products, and assays for cartilage degradation using the antibodies and linear peptides.

| α1(II)N Telopeptide Sequence[1] | SEQ ID NO | Body Fluid[2] | | |
|---|---|---|---|---|
| | | Synovial fluid | Blood | Urine |
| DEKAGGA | 21 | N | N | N + M |
| DEKAGGAQ | 22 | N | N | N + M |
| DEKAGGAQL | 23 | N | N | N + M |
| FDEKAGGA | 24 | N | N | N + M |
| FDEKAGGAQ | 25 | N | N | N + M |
| FDEKAGGAQL | 26 | N | N | N + M |
| GGFDEKAGGAQLG | 27 | — | M | — |
| JMAGGFDEKAGGAQLG | 28 | — | M | — |
| JMAGGFDEKAGGAQLGV | 29 | N | N | — |
| FDEKAGGAQLGV | 30 | N | N | — |
| DEKAGGAQLGV | 31 | N | N | — |

[1]J = pyroglutamic acid, i.e., wholly cyclized pyrrolidone carboxylic acid (5-oxo-2-pyrrolidinecarboxylic acid).
[2]Cartilage Source:
N = non-mineralized cartilage;
M = mineralized cartilage;
N + M = total cartilage degradation; and
— = absent or only trace amounts.

The telopeptide sequences represented by SEQ ID NOS 21–23 result from metalloproteinase (MMP) cleavage of the F-D bond at the amino end of the α1(II)N telopeptide, in combination with MMP cuts of the A-Q, Q-L, or L-G bonds at the carboxy end of the telopeptide. SEQ ID NOS 24–26 represent related telopeptides from MMP cleavage between the G-F bond at the amino end. The amino and carboxy ends of the longer telopeptides (SEQ ID NOS 22–26) are generally metabolized further in the lymph nodes, liver, and/or kidney. As a result, the principal col2NTx degradation products in urine are cross-linked DEKAGGA and FDEKAGGA.

The telopeptide sequences represented by SEQ ID NOS 27–28 result from cathepsin K cleavage of the G-V bond at the carboxy end of the telopeptide, in combination with cathepsin K cleavage of the A-G bond at the amino end of the telopeptide in the case of SEQ ID NO 27. In the case of SEQ ID NO 28 the amino terminal J residue is blocked. Higher than normal levels of cross-linked GGFDEKAGGAQLG and QMAGGFDEKAGGAQLG in blood can indicate mineralized cartilage degradation associated with active osteophyte formation in osteoarthritis. Proteases in the kidney and/or liver remove the carboxy-terminal G residue before release into the urine.

The telopeptides represented by SEQ ID NOS 29–31 result from metalloproteinase cleavage of the V-M bond at the carboxy end of the telopeptide, in combination with MMP cleavage of the G-F or F-D bond at the amino end of the telopeptide in the case of SEQ ID NOS 30–31. Larger degradation products comprising SEQ ID NOS 29–31 plus some additional helical sequence(s) may also be present in synovial fluid and blood. These cross-linked telopeptides are generally metabolized further in the lymph nodes, liver, and/or kidney, and consequently occur only in trace amounts in urine.

As indicated above, cross-linked α1(II)N telopeptides represented by SEQ ID NOS 27–31 are produced at the site(s) of cartilage degradation but degraded further during passage through the lymph nodes, liver, and/or kidney. The resulting smaller degradation products have two telopeptide components that may be independently selected from among SEQ ID NOS 21–26. Higher than normal levels of these degradation products in urine indicate total cartilage degradation that may correlate with rheumatoid arthritis, osteoarthritis, and other arthritides.

Thus the invention provides, in a first embodiment, an improved method of analyzing a body fluid sample for the presence of an analyte indicative of a physiological condition, including the steps of contacting the body fluid sample with an antibody which binds to the analyte, detecting binding of the antibody in the body fluid sample, and correlating any detected binding to the physiological condition, the improvement comprising contacting a serum sample with an antibody which binds to

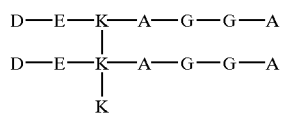

but not to

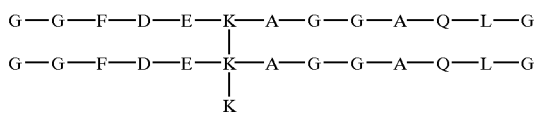

wherein K-K-K is hydroxylysyl pyridinoline or lysyl pyridinoline, and correlating any detected binding to resorption of non mineralized type II collagen in vivo.

In a second embodiment, the invention provides an improved method of analyzing a body fluid sample for the presence of an analyte indicative of a physiological condition, including the steps of contacting the body fluid sample with an antibody which binds to the analyte, detecting binding of the antibody in the body fluid sample, and correlating any detected binding to the physiological condition, the improvement comprising contacting a serum sample with an antibody which binds to

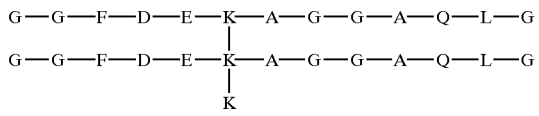

but not to

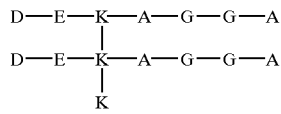

wherein K-K-K is hydroxylysyl pyridinoline or lysyl pyridinoline, and correlating any detected binding to resorption of mineralized type II collagen in vivo.

In a third embodiment, the invention provides an improved method of analyzing a body fluid sample for the presence of an analyte indicative of a physiological condition, including the steps of contacting the body fluid sample with an antibody which binds to the analyte, detecting binding of the antibody in the body fluid sample, and correlating any detected binding to the physiological condition, the improvement comprising contacting a urine sample with an antibody which binds to

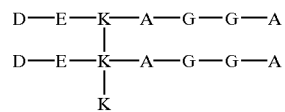

but not to

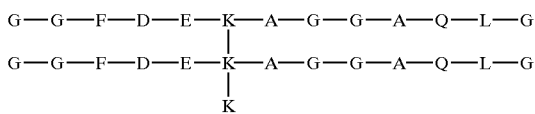

wherein K-K-K is hydroxylysyl pyridinoline or lysyl pyridinoline, and correlating any detected binding to resorption of both non-mineralized and mineralized type II collagen in vivo.

In a fourth embodiment, the invention provides an improved method of analyzing a body fluid sample for the presence of an analyte indicative of a physiological condition, including the steps of contacting the body fluid sample with an antibody which binds to the analyte, detecting binding of the antibody in the body fluid sample, and correlating any detected binding to the physiological condition, the improvement comprising contacting a serum sample with a first antibody which binds to

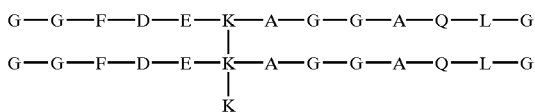

but not to

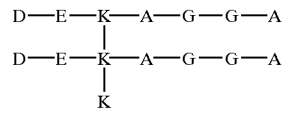

and contacting the serum sample with a second antibody which binds to

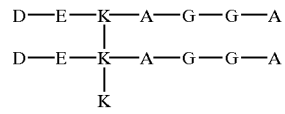

but not to

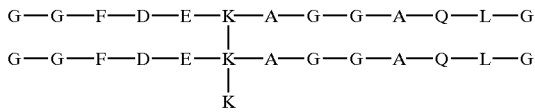

total detected binding of the first and second antibodies to resorption of both mineralized and non-mineralized type II collagen in vivo.

In a fifth embodiment, the invention provides an improved method of analyzing a body fluid sample for the presence of an analyte indicative of a physiological condition, including the steps of contacting the body fluid sample with an antibody which binds to the analyte, detecting binding of the antibody in the body fluid sample, and correlating any detected binding to the physiological condition, the improvement comprising contacting a serum sample with a first antibody which binds to

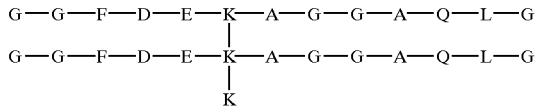

but not to

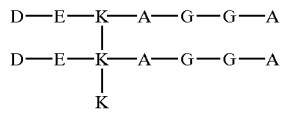

and contacting a urine sample with a second antibody which binds to

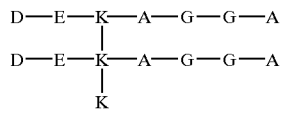

but not to

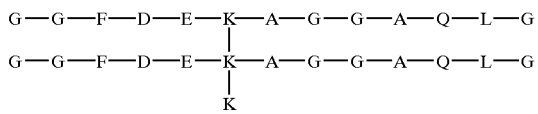

wherein K-K-K is hydroxylysyl pyridinoline or lysyl pyridinoline, and correlating any detected binding of the first antibody to resorption of mineralized type II collagen in vivo, and any detected binding of the second antibody to resorption of both mineralized and non-mineralized type II collagen in vivo.

The term "antibody" in this disclosure is meant to encompass polyclonal antibodies, monoclonal antibodies, and antigen-binding fragments thereof. Such EKGPDPLQ-binding and EKGPDP-binding antibodies, or GGFDEKAGGAQLG-binding and DEKAGGA-binding antibodies, can be produced by standard methods well known in the art. A representative protocol follows.

EKGPDPLQ hybridoma development: Female RFB/DnJ mice are injected intraperitoneal (ip) with an emulsion of complete Freund's adjuvant and EKGPDPLQ synthetic peptide cross-linked to the carrier protein keyhole limpet hemacyanin (KLH) via glutaraldehyde (KLH-EKGPDPLQ). One month later a booster injection of KLH-EKGPDPLQ is given ip in an emulsion with incomplete Freund's adjuvant. Approximately eight weeks later the mice are sacrificed and splenocytes fused, by polyethylene glycol, to the FOX-NY murine myeloma cell line (ATCC CRL-1732). Fusion cells are grown in 96-well plates in selection media containing adenine, aminopterin and thymidine (AAT).

Approximately one week after fusion hybridoma colony culture supernatants are tested in ELISA for reactivity to the EKGPDPLQ synthetic peptide cross-linked via glutaraldehyde to bovine serum albumin (BSA-EKGPDPLQ). Hybridoma colonies producing antibody reactive with BSA-EKGPDPLQ are secondarily tested for specificity of reaction in ELISA against other synthetic peptide sequences. Among those tested are EKGPDP synthetic peptide cross-linked to BSA via glutaraldehyde (BSA-EKGPDP). Hybridoma colonies that react positively to BSA-EKGPDPLQ and negatively to BSA-EKGPDP are cryopreserved. Representative hybridomas are cloned to monoclonality by the limited dilution method.

In competition ELISA, human serum specimens as well as soluble BSA-EKGPDPLQ are found to compete with solid phase BSA-EKGPDPLQ for candidate antibodies.

A cathepsin K digest of type II collagen can also be prepared for immunization and screening purposes. Proteoglycans are extracted from a tissue sample of human articular cartilage with a protein denaturant, such as 4 M guanidine HCl. The residue is washed with water and digested with recombinant cathepsin K (37° C., pH 5.8). The digest is fractionated by high performance liquid chromatography, for example by reverse phase, and fractions containing pyridinoline cross-links are monitored by fluorescence emission at 390 nm (297 nm excitation). The fluorescent fraction containing the cross-linked C-telopeptides of sequence EKGPDPLQ is identified by N-terminal sequence analysis. This fraction can be used for screening purposes and for validation of antibody specificity.

The subject antibodies can be employed in a variety of immunoassay formats that are well known in the art. For example, see: Harlow & Lane, Antibodies: A Laboratory Manual, Cold Spring Harbor Laboratory, pp. 553–612, 1988; Principles and Practice of Immunoassay, Price & Newman (Eds.), Stockton Press, 1991; and Immunoassay, Diamandis & Christopoulos (Eds.), Academic Press, 1996.

Type III Collagen

This invention provides antibodies directed against cross-linked amino-telopeptide degradation products of type III collagen, as well as linear peptides (SEQ ID NOS 33–37) synthesized to match the telopeptide components of the degradation products, and assays for type III collagen degradation using the antibodies and linear peptides. For reference, the native α1(III)N telopeptide has the following amino acid sequence: JYDSYDVKSGVAVGGLAG (SEQ ID NO 32).

| α1(III)N Telopeptide Sequence[1] | SEQ ID NO | Body Fluid[2] | | |
|---|---|---|---|---|
| | | Synovial fluid | Blood | Urine |
| DVKSGVAVGG | 33 | x | x | x |
| YDVKSGVAVGG | 34 | x | x | x |
| SYDVKSGVAVGG | 35 | x | x | x |
| DSYDVKSGVAVGG | 36 | x | x | x |
| JYDSYDVKSGVAVGG | 37 | x | x | x |
| proQYDSYDVKSGVAVGG | 38 | x | x | x |

[1]J = pyroglutamic acid, i.e., wholly cyclized pyrrolidone carboxylic acid (5-oxo-2-pyrrolidinecarboxylic acid).
[2]x = present.

The preferential site for initial metalloproteinase (MMP) cleavage is the G-L bond near the carboxy end of the α1(III)N telopeptide. Thus, the cross-linked col3NTx degradation products in body fluids all share the distinctive-KSGVAVGG neoepitope (SEQ ID NO 45).

The telopeptides represented by SEQ ID NOS 33–36 result, for example, from metalloproteinase (MMP) cleavage of the Y-D, S-Y, D-S, or Y-D bonds at the amino end of the telopeptide, in combination with the G-L cleavage at the carboxy end.

The telopeptide represented by SEQ ID NO 37 retains the amino terminal J residue. Larger variants have the intact globular N-propeptide, or a fragment thereof, still retained to the amino terminus (wherein the terminal residue is Q). These larger variants are collectively indicated in the Table above as "proQYDSYDVKSGVAVGG". Even these largest forms containing N-propeptide remnants pass into urine. All are preferably assayed using an antibody directed against the cross-linked -KSGVAVGG epitope. Assay for these fragments by this preferred epitope provides an index of structural type III collagen degradation rather than new synthesis.

This invention also provides antibodies directed against cross-linked carboxy-telopeptide degradation products of type III collagen, as well as linear peptides (SEQ ID NOS 39–44) synthesized to match the telopeptide components of the degradation products, and assays for type III collagen degradation using the antibodies and linear peptides. For reference, the native α1(III)C telopeptide has the following amino acid sequence: GGVGAAAIAGIGGEKAGGFAPYY (SEQ ID NO 38).

| α1(III)C Telopeptide Sequence | SEQ ID NO | Body Fluid[1] | | |
|---|---|---|---|---|
| | | Synovial fluid | Blood | Urine |
| EKAGGF | 39 | — | — | x |
| IGGEKAGG | 40 | x | x | x |
| IGGEKAGGF | 41 | x | x | — |
| IAGIGGEKAGG | 42 | x | x | — |
| IAGIGGEKAGGF | 43 | x | x | — |

[1]x = present; and — = absent or only trace amounts.

The preferential site for initial metalloproteinase (MMP) cleavage is the A-I bond near the amino end of the α1(III)C telopeptide. The telopeptides represented by SEQ ID NOS 43 and 42 result from MMP cleavage of the F-A or G-F bonds at the carboxy end of the telopeptide, in combination with the A-I cleavage at the amino end. The telopeptide represented by SEQ ID NO 41 results from further processing by MMP cleavage of the G-I bond at the amino end of the telopeptide. These degradation products are present in blood and synovial fluid but are absent or found only in trace amounts in urine. Additional cleavages in the kidney result in smaller fragments in the urine.

The telopeptide represented by SEQ ID NO 40 results from MMP cleavage of the G-I bond at the amino end of the telopeptide, in combination with the G-F cleavage at the carboxy end. This cross-linked degradation product is found in all body fluids.

The telopeptide represented by SEQ ID NO 39 results from cleavage by kidney proteases of the G-E bond at the amino end of the telopeptide. This cross-linked degradation product is therefore found in significant amounts only in urine. Even smaller cross-linked peptides, including those with telopeptide component(s) EKAGG (SEQ ID NO 44), also appear in urine through the action of proteases in the kidney.

While the invention has been described in conjunction with preferred embodiments, one of ordinary skill after reading the foregoing specification will be able to effect various changes, substitutions of equivalents, and alterations to the subject matter set forth herein. Hence, the invention can be practiced in ways other than those specifically described herein.

The embodiments of the invention in which an exclusive property or privilege is claimed are defined as follows:

1. A synthetic peptide selected from among DVKSGVAVGG (SEQ ID NO 33), YDVKSGVAVGG (SEQ ID NO 34), SYDVKSGVAVGG (SEQ ID NO 35), DSYDVKSGVAVGG (SEQ ID NO 36), JYDSYDVKSGVAVGG (SEQ ID NO 37), and KSGVAVGG (SEQ ID NO 45).

* * * * *

UNITED STATES PATENT AND TRADEMARK OFFICE
CERTIFICATE OF CORRECTION

PATENT NO. : 6,602,980 B1
DATED : August 5, 2003
INVENTOR(S) : D.R. Eyre

It is certified that error appears in the above-identified patent and that said Letters Patent is hereby corrected as shown below:

Title page,
Item [63], Related U.S. Application Data, "Continuation of application No. 09/385,740 filed on Aug. 30, 1999, now Pat. No. 6,348,320, which is a continuation of application No. 09/335,098, filed on Jun. 17, 1999, now Pat. No. 6,255,056." should read -- Continuation-in-part of application No. 09/385,740, filed on Aug. 30, 1999, now Pat. No. 6,348,320, which is a continuation-in-part of application No. 09/335,098, filed on Jun. 17, 1999, now Pat. No. 6,255,056. --

Item [60], "Provisional application No. 60/142,675, filed on Jul. 7, 1999, provisional application No. 60/142,274, filed on Jul. 2, 1999, and provisional application No. 60/141,574, filed on Jun. 29, 1999." should read -- Provisional application No. 60/142,675, filed on Jul. 7, 1999, provisional application No. 60/142,274, filed on Jul. 2, 1999, provisional application No. 60/141,574, filed on Jun. 29, 1999, and provisional application No. 60/089,823, filed on Jun. 19, 1998. --

Item [56], References Cited, OTHER PUBLICATIONS, "Seibel, M.J.," reference, "potentialle ... Marker des Bindegewebs-,
Knorpe-
1-und" should read -- potentielle . . . "Marker" des
Bindegewebs-, Knorpel- und --;
"Niemelá," should read -- Niemelä, --;
"Hasselbach," should read -- Hasselbalch, --; and
"Atley, L.M. et al.," reference, "Telopeptide" should read -- Telopeptides --

Column 1,
Lines 8-9, "6,255,
056," should not break

Column 7,
Line 36, "non mineralized" should read -- non-mineralized --

UNITED STATES PATENT AND TRADEMARK OFFICE
CERTIFICATE OF CORRECTION

PATENT NO. : 6,602,980 B1
DATED : August 5, 2003
INVENTOR(S) : D.R. Eyre

It is certified that error appears in the above-identified patent and that said Letters Patent is hereby corrected as shown below:

Column 8,
Line 62, at the beginning of the paragraph, before the text "total detected binding" insert -- where K-K-K is hydroxylysyl pyridinoline or lysyl pyridinoline, and correlating the --

Signed and Sealed this

Sixth Day of January, 2004

JAMES E. ROGAN
*Director of the United States Patent and Trademark Office*